United States Patent
Fulkerson

(10) Patent No.: US 10,288,612 B2
(45) Date of Patent: May 14, 2019

(54) METHODS FOR DIAGNOSING AND TREATING EOSINOPHILIC ESOPHAGITIS

(71) Applicant: Children's Hospital Medical Center, Cincinnati, OH (US)

(72) Inventor: Patricia C. Fulkerson, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 43 days.

(21) Appl. No.: 15/358,864

(22) Filed: Nov. 22, 2016

(65) Prior Publication Data

US 2017/0199191 A1 Jul. 13, 2017

Related U.S. Application Data

(60) Provisional application No. 62/275,959, filed on Jan. 7, 2016.

(51) Int. Cl.
| | |
|---|---|
| *G01N 33/569* | (2006.01) |
| *A23L 33/20* | (2016.01) |
| *A61K 31/00* | (2006.01) |
| *G01N 33/68* | (2006.01) |

(52) U.S. Cl.
CPC ........ *G01N 33/56972* (2013.01); *A23L 33/20* (2016.08); *A61K 31/00* (2013.01); *G01N 33/6893* (2013.01); *G01N 2800/06* (2013.01); *G01N 2800/24* (2013.01)

(58) Field of Classification Search
None
See application file for complete search history.

(56) References Cited

PUBLICATIONS

Konikoff et al (Clin Gastroenterol Hepatol 4:1328-1336, 2006—Abstract only).*
Mori et al (J Exp Med 206:183-193, 2008).*
Kay (Trends in Molecular Med 11:148-152, 2005).*
Makowska et al (Ann Allergy Asthma Immunol 101:402-406, 2008).*
Alexander et al (Gastroenterol Hepatol 7:59-61, 2011).*
Konikoff et al (Clip Gastroenterol Hepatol 4:1328-1336, 2006) (Year: 2006).*
Blanchard, C., et al., "A striking local esophageal cytokine expression profile in eosinophilic esophagitis," J Allergy Clin Immunol, 2011, 127(1):208-17, 217 e1-7, 20 pgs.
Bullock, J.Z., et al., "Interplay of Adaptive Th2 Immunity with Eotaxin-3/C—C Chemokine Receptor 3 in Eosinophilic Esophagitis," Journal of Pediatric Gastroenterology and Nutrition, 2007, 45:22-31, 10 pgs.
Henderson, C.J., et al., "Comparative Dietary Therapy Effectiveness in Remission of Pediatric Eosinophilic Esophagitis," J Allergy Clin Immunol, 2012,129(6):1570-8, 22 pgs.
Konikoff, M.R., et al., "Potential of Blood Eosinophils, Eosinophil-Derived Neurotoxin, and Eotaxin-3 as Biomarkers of Eosinophilic Esophagitis," Clin Gastroenterol Hepatol, 2006, 4(11):1328-36, 9 pgs.
Liacouras, C.A., et al., "Eosinophilic esophagitis: Updated consensus recommendations for children and adults," J Allergy Clin Immunol, 2011, 128(1):3-20, 24 pgs.
Makowska, J., et al., "Recruitment of CD34+ progenitor cells into peripheral blood and asthma severity," Ann Allergy Asthma Immunol, 2008, 101:402-406, 5 pgs.
Martin, L.J., et al., "Pediatric Eosinophilic Esophagitis Symptom Scores (PEESS® v2.0) identify histologic and molecular correlates of the key clinical features of disease," J Allergy Clin Immunol, 2015, 135:1519-28, 22 pgs.
Mori, Y., et al., "Identification of the human eosinophil lineage-committed progenitor: revision of phenotypic definition of the human common myeloid progenitor," J Exp Med, 2009, 206(1):183-93, 11 pgs.
Sehmi, R., et al., "Increased Levels of CD34+ Hemopoietic Progenitor Cells in Atopic Subjects," Am J Respir Cell Mol Biol, 1996, 15:645-54, 11 pgs.
Smith, S.G., et al., "Thymic stromal lymphopoietin and IL-33 modulate migration of hematopoietic progenitor cells in patients with allergic asthma," J Allergy Clin Immunol, 2015, 135(6):1594-602, 9 pgs.
Warners, M.J., et al., "Elimination and elemental diet therapy in eosinophilic oesophagitis," Clinical Gastroenterology, Oct. 2015, 29(5):793-803, 11 pgs.

\* cited by examiner

*Primary Examiner* — Craig D Ricci
(74) *Attorney, Agent, or Firm* — Frost Brown Todd LLC

(57) ABSTRACT

Disclosed are methods of diagnosing and treating a subject with active or inactive eosinophilic esophagitis (EoE). The methods may include the steps of detecting whether a level of eosinophil lineage-committed progenitor (EoP) is elevated in a blood sample obtained from a subject, diagnosing the subject with active EoE when an EoP level in the sample is elevated above a pre-determined cut-off value and diagnosing the subject with inactive EoE when the EoP level in the sample is below a pre-determined cut-off value; and treating the subject diagnosed with active EoE. Kits related to same are also disclosed.

2 Claims, 4 Drawing Sheets

METHODS FOR DIAGNOSING AND TREATING EOSINOPHILIC ESOPHAGITIS

CROSS-REFERENCE TO RELATED APPLICATIONS

This application claims priority to and benefit of U.S. Provisional Patent Application No. 62/275,959, to Fulkerson, filed on Jan. 7, 2016, entitled "Eosinophil progenitor levels in active pediatric Eosinophilic Esophagitis" in its entirety and for all purposes.

STATEMENT REGARDING FEDERALLY-SPONSORED RESEARCH

This invention was made with government support under AI093673, AI117804, and DK078392 awarded by the National Institutes of Health. The government has certain rights in the invention.

BACKGROUND

Eosinophilic esophagitis (EoE) is a chronic, food antigen-driven gastrointestinal disease characterized by marked esophageal eosinophilia. CCL26 (eotaxin-3) levels mediate eosinophil tissue recruitment [1, 2], and eosinophil tissue counts serve as the basis for diagnosis [3]. Currently, EoE treatment efficacy is often determined via invasive serial endoscopies with esophageal biopsies; thus, there is a compelling need to develop novel and less-invasive blood-based biomarkers to evaluate EoE disease activity.

BRIEF SUMMARY

Disclosed are methods of diagnosing and treating a subject with active or inactive eosinophilic esophagitis (EoE). The methods may include the steps of detecting whether a level of eosinophil lineage-committed progenitor (EoP) is elevated in a blood sample obtained from a subject, diagnosing the subject with active EoE when an EoP level in the sample is elevated above a pre-determined cut-off value and diagnosing the subject with inactive EoE when the EoP level in the sample is below a pre-determined cut-off value; and treating the subject diagnosed with active EoE. Kits related to same are also disclosed.

BRIEF DESCRIPTION OF THE DRAWINGS

FIG. 1A Median absolute EoP levels in patients with active versus inactive EoE are shown. (For all box plots, Box=25-75$^{th}$ percentile, whiskers=minimum to maximum values, all points shown, each point represents an individual patient) FIG. 1B. Median absolute EoPs correlate with peak esophageal eosinophils (Spearman). FIG. 1C. Receiver operating characteristic analysis of the ability of EoP levels to discriminate between patients with and without active EoE. The solid diagonal line indicates values that have no discriminatory value. FIG. 1D. Comparison of median EoP levels in active EoE divided into two groups, restricted diet (food trials) versus unrestricted diet, is shown. FIG. 1E. Median values of peak esophageal eosinophils in active EoE divided into two groups, restricted diet (food trials) versus unrestricted diet, are shown.

DETAILED DESCRIPTION

Definitions

Figure 1:
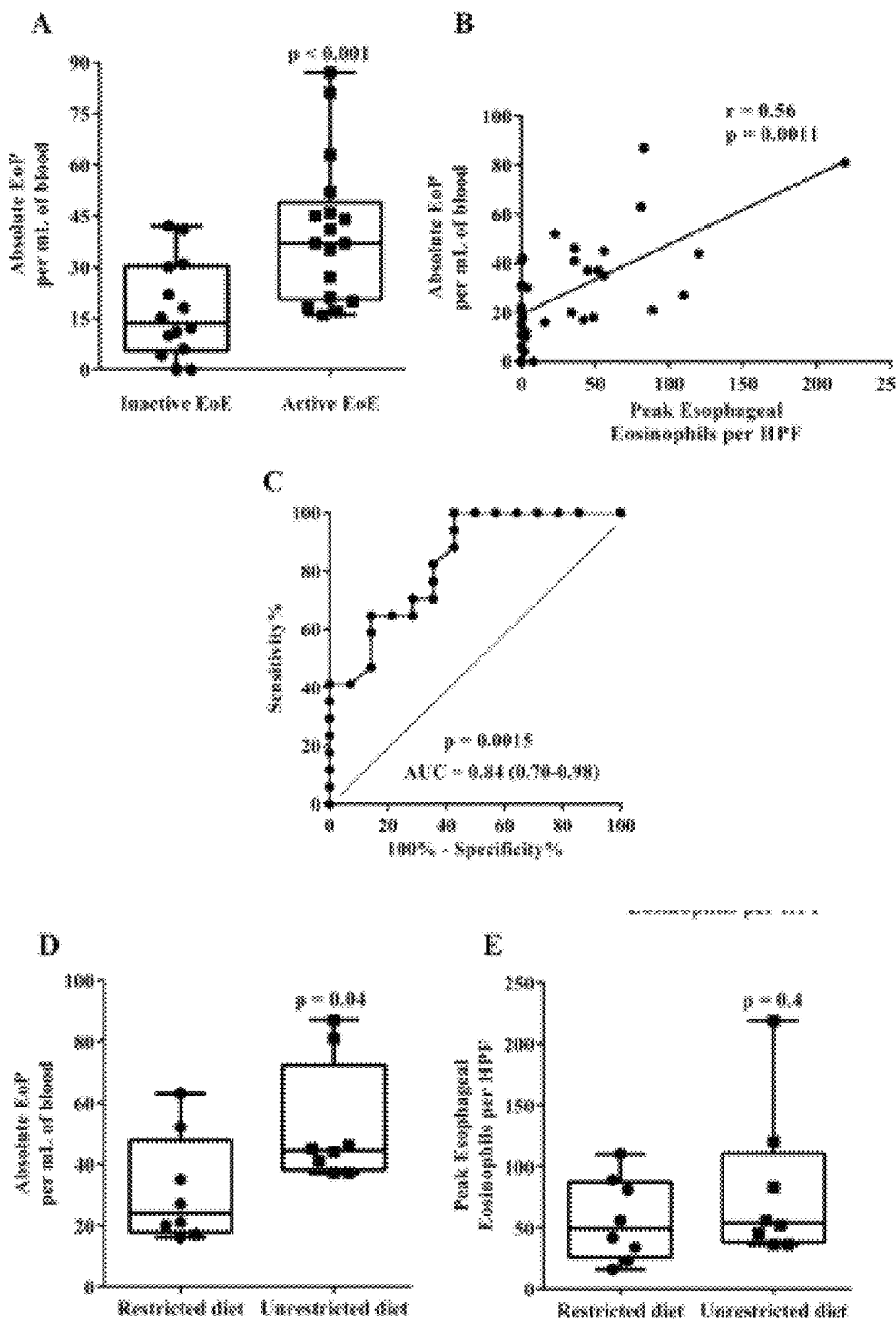
FIG. 1A-1E.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

Though peripheral blood eosinophil counts moderately correlate with esophageal tissue eosinophil levels, their relationship is not sufficient to serve as a clinically useful biomarker [4]. Similar to the mature eosinophil, the lineage-committed eosinophil progenitor (EoP) is mobilized during allergic disease [5]. EoP frequency is increased in the peripheral blood of adult patients with asthma in response to allergen challenge [6, 7]. Also, EoP levels are increased in the lung tissue and sputum of allergen-challenged patients with asthma, suggesting a direct contribution to tissue eosinophilia via in situ differentiation after migration from the peripheral blood [6, 8]. Notably, peripheral blood EoP levels correlate with the severity of asthma in adults, advancing the concept of the EoP as a clinically useful biomarker [6]. No clinical studies to date have measured EoP levels in EoE. Applicant hypothesized that EoP levels would be increased in the peripheral blood of pediatric patients with active EoE disease and would correlate sufficiently with the level of mature eosinophils in the esophagus to serve as a relevant biomarker for EoE disease activity. Applicants have found that Eosinophil progenitor (EoP) levels are increased in the blood of pediatric patients with active eosinophilic esophagitis (EoE), and that blood EoP levels can be successfully used as a novel, blood-based biomarker to monitor EoE disease activity.

Prior to Applicant's discovery, measurements of EoP levels in the blood were previously only determined in adult asthma. Measurement of EoP blood levels had never been used in EoE or in children because it was believed that it would not be possible to get an accurate reading from a small volume of blood, in the range of 5 ml or less. Applicant has found that, not only can a reading be obtained, but that the data obtained is surprisingly accurate.

Applicant has further found that the disclosed methods further allow for management of dietary control of EoE. The EoP test is a technique using flow cytometry to identify EoPs by surface markers in a small volume of blood and then calculate the frequency (EoP per µL) can be used to determine when restricted foods can be reintroduced into the diet of an EoE patient. For example, if the EoP test results in an "inactive reading," it can be determined that the permitted foods are likely not contributing factors to EoE. Following a negative reading, the patient can resume intake of other potentially restricted food groups, and the test can be repeated to determine if the newly introduced foods are contributing to EoE. Accordingly, administration of the EoE test can facilitate management of EoE aggravated or caused by diet.

In one aspect, a method of diagnosing and treating a subject with active or inactive eosinophilic esophagitis (EoE) is disclosed. The method may comprise the step of detecting whether a level of eosinophil lineage-committed progenitor (EoP) is elevated in a blood sample obtained from the subject. The blood sample may have a volume of less than about 5, or less than about 4 or less than about 3 mLs. The subject may be diagnosed with active EoE when the measured EoP level in the sample is elevated above a pre-determined cut-off value or diagnosed with inactive EoE when the EoP level in the sample is below a pre-determined cut-off value. The method may further comprise the step of treating the subject diagnosed with active EoE.

In one aspect, the pre-determined cut-off value may be about 15 EoPs per mL (esophageal eosinophils/HPF) of blood, or, in certain aspects, about 15.5 EoPs per mL.

In one aspect, when the EoP level is below about 15 EoPs per mL, or about 15.5 EoPs per mL, of blood, the subject is diagnosed with inactive EoE.

In one aspect, the treatment step may comprise administration of steroids, administration of a proton-pump inhibitor, withdrawal of one or more food types, an amino-acid based formula diet, or a combination thereof.

In one aspect, the methods may be used to identify a food sensitivity in a subject. When active EoE is diagnosed, a food type may be eliminated from the diet of the subject diagnosed with active EoE. After a period of time a second sample may be obtained from the subject post-elimination. If EoP is not detected, then the subject is diagnosed with a sensitivity to the eliminated food type. The subject may be treated by placing the subject on a restricted diet. The restricted diet is typically one in which the previously-eliminated food is restricted from the diet.

In one aspect, the restricted diet may be an elimination of one or more foods selected from cow's milk, egg, soy, wheat, peanuts/tree nuts, seafood. In certain aspects, all six foods are eliminated. Guidelines for an elimination diet are described in Liacouras et al 2011 ("Eosinophilic esophagitis: Updated consensus recommendations for children and adults" Liacouras, C. A., et al., Journal of Allergy and Clinical Immunology, July 2011, Vol. 128, Issue 1, pp 3-20.e6, DOI: http://dx.doi.org/10.1016/j.jaci.2011.02.040). Diet therapy is described in Warners et al 2015 ("Elimination and elemental diet therapy in eosinophilic oesophagitis," M. J. Warners et al., *Clinical Gastroenterology*, October 2015, Vol. 29, Issue 5, pp 793-803, DOI: http://dx.doi.org/10.1016/j.bpg.2015.06.013.

In one aspect, a method of diagnosing and treating a subject with a food allergy that is associated with active eosinophilic esophagitis (EoE) is disclosed. The method may comprise the steps of detecting whether a level of eosinophil lineage-committed progenitor (EoP) is elevated in a blood sample obtained from a subject, wherein a food has been re-introduced into the subject's diet following a restricted diet;

diagnosing the subject with a food allergy if the EoP level in the sample is elevated above a pre-determined cut-off value after reintroduction of the previously restricted food; and treating the subject diagnosed with the food allergy to the reintroduced food, wherein the treatment comprises maintaining the restricted diet.

In one aspect, the pre-determined cut-off value may be about 15 EoPs per mL (esophageal eosinophils/HPF) of blood.

In one aspect, where the EoP level is below about 15 EoPs per mL of blood, the subject is diagnosed with inactive EoE.

In one aspect, a kit is disclosed. The kit may comprise a test for assaying the level of EoP in the blood of a subject; and instructions for diagnosing a subject with active or inactive eosinophilic esophagitis (EoE). The kit may further comprise a label instructing the user to use the kit for diagnosis of active or inactive EoE and/or a food sensitivity.

Examples

Peripheral blood samples for EoP enumeration were obtained from consented pediatric patients (Table 1) undergoing endoscopy for evaluation of EoE at the Cincinnati Center for Eosinophilic Disorders (CCED, Cincinnati Children's Hospital Medical Center [CCHMC]). Included subjects were ages 1-18 years and had a diagnosis of EoE. Patients met the consensus criteria for EoE and failed proton pump inhibitor (PPI) therapy, which serves as part of the diagnostic criteria of EoE [3]. Patients were excluded if other inflammatory gastrointestinal diseases, such as Crohn's disease or other eosinophilic gastrointestinal diseases, were present or if they had used systemic steroids, such as prednisone or other immune modulators, in the previous two months. Demographic and medical record information for each participant was maintained in a CCED research database and reviewed to obtain relevant patient information.

Figure 2:
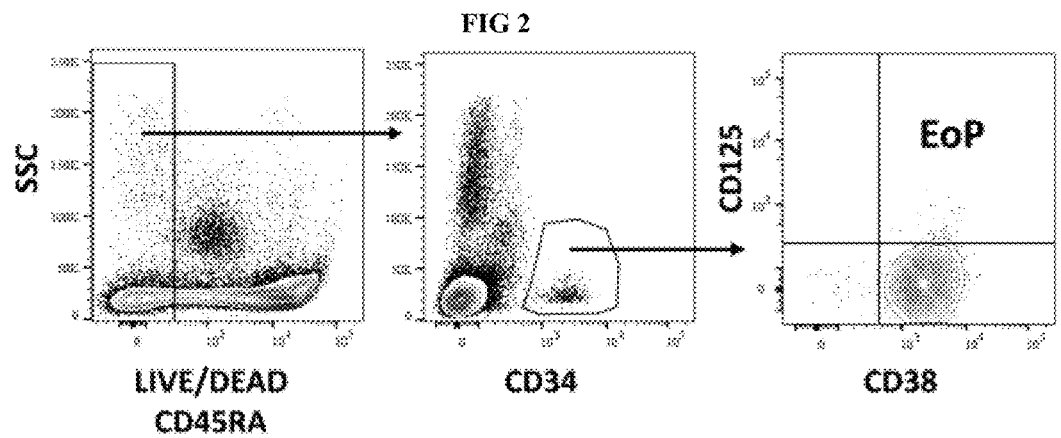
FIG. 2. Gating strategy for EoPs. Live CD45RA-negative cells were gated for CD34-positive events. This population was gated for CD38 and CD125 (IL-5Rα), with double-positive events being considered EoPs. EoP levels are expressed in absolute numbers per milliliter of blood.
Figure 3:
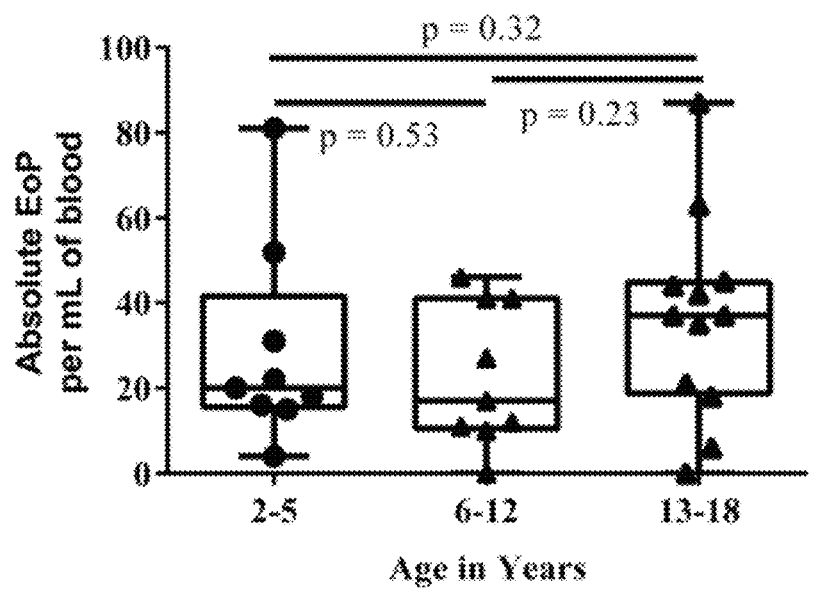
FIG. 3. Absolute EoPs per mL stratified by patient age are shown. Significance levels are indicated the bars span the different groups.
Figure 4:
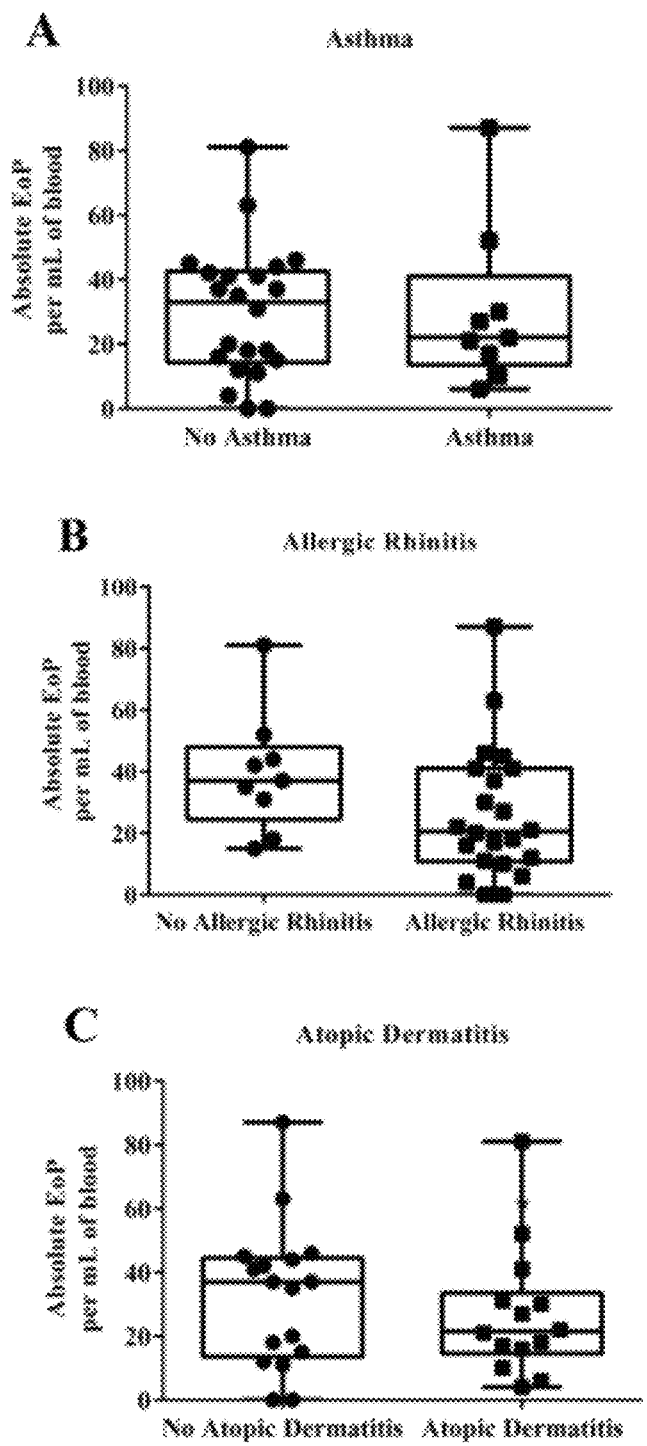
FIG. 4. Median of EoP levels from EoE patients with and without asthma, allergic rhinitis, or atopic dermatitis (Box=25-75$^{th}$ percentile, whiskers=minimum to maximum values, all values shown, each circle or square represents an individual patient).
Figure 5:
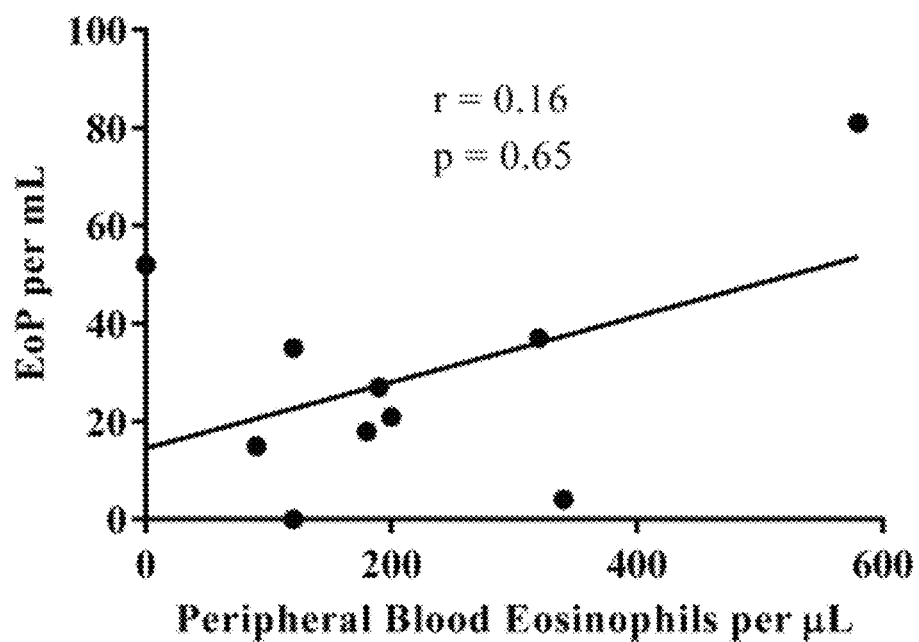
FIG. 5. Spearman correlation between peripheral blood eosinophils (absolute count/µL) and peripheral blood EoP (absolute count/mL) is shown.

Peripheral blood mononuclear cell (PBMC) isolation and flow staining were performed as detailed in the online repository. EoPs were identified as a subpopulation of live PBMCs using the gating strategy in FIG. 2 in the online repository. Subsequently, patients were divided into two groups on the basis of their esophageal eosinophil levels, active EoE (n=17; median age 14.0 [interquartile range 5.5-16.5] years, peak esophageal eosinophils ≥15 eosinophils/high-power microscopic field [hpf], median 52.0 [interquartile range, 36.0-86.0] eosinophils/hpf) and inactive EoE (n=14; median age 7.5 [3.0-12.5] years, peak esophageal eosinophils <15 eosinophils/hpf, median 0.5 [0.0-3.0] eosinophils/hpf). Patient age between the inactive and active disease groups was not significantly different (p=0.08), and median EoP levels did not vary by age (FIG. 3 in the online repository).

Five milliliters (mL) of whole blood is collected in tubes with heparin anti-coagulant and processed immediately. Five mL of phosphate-buffered saline (PBS) solution is added to the whole blood and mixed gently before carefully layering over Ficoll Paque Plus in a 50-mL tube. The tube with diluted blood and Ficoll Paque Plus is centrifuged at 400×g for 30 minutes with the brake off. The interphase containing the mononuclear cell layer is removed, washed in 40 mL of PBS and centrifuged at 300×g for 10 minutes. The mononuclear cell pellet is then resuspended in PBS (with added 0.5% bovine serum albumin and 2 mM ethylenediaminetetraacetic acid) and stained at room temperature with the following antibodies: CD45RA-APC Cy7 (final concentration 1 μg/mL), CD38-FITC (final concentration 4 μg/mL), CD34-BV421 (final concentration 500 ng/uL), and CD125-PE (final concentration 2 μg/mL) and a viability stain. Accucount Blank Particles (50 μL per tube) were then added to each tube. For the flow data acquisition, the beads are used as a counting gate within the SCC/FSC parameter and 10,000 events in the bead gate are acquired. Fluorescence minus one controls are utilized to set gates for flow analysis. To identify EoPs in the mononuclear cells, live CD45RA-negative cells were gated for CD34-positive events. This

TABLE 1

Table I. Patient Characteristics

| Sex | Age[a] (years) | Atopic Phenotype[b] | Therapy[c] | PPI[b] | Peak Esophageal Eosinophil Count (per hpf) | Blood Eosinophil Progenitor Count (per mL blood) |
|---|---|---|---|---|---|---|
| Inactive EoE (n = 14) | | | | | | |
| F | 8 | AR+ AD− As− | Food Trials | Yes | 0 | 0 |
| F | 18 | AR+ AD+ As+ | Food Trials | Yes | 0 | 6 |
| F | 9 | AR+ AD− As− | Food Trials | Yes | 0 | 11 |
| M | 3 | AR+ AD+ As+ | Food Trials | Yes | 0 | 22 |
| M | 3 | AR− AD− As− | Food Trials | Yes | 1 | 18 |
| F | 6 | AR+ AD+ As+ | Food Trials | Yes | 3 | 10 |
| M | 2 | AR+ AD+ As− | Food Trials | Yes | 2 | 4 |
| M | 3 | AR− AD− As− | Food Trials | Yes | 0 | 15 |
| F | 3 | AR− AD+ As− | Food Trials | No | 0 | 31 |
| M | 11 | AR+ AD− As− | Food Trials | Yes | 3 | 12 |
| M | 14 | AR− AD− As− | Food Trials | Yes | 1 | 42 |
| F | 12 | AR+ AD+ As− | Food Trials | Yes | 0 | 41 |
| F | 7 | AR+ AD+ As+ | Food Trials | No | 4 | 30 |
| M | 15 | AR+ AD− As− | Food Trials and Steroids | Yes | 8 | 0 |
| Active EoE (n = 17) | | | | | | |
| M | 3 | AR+ AD+ As− | Food Trial | Yes | 16 | 16 |
| M | 15 | AR− AD− As− | Food Trial | No | 56 | 35 |
| M | 7 | AR+ AD+ As+ | Food Trial | Yes | 110 | 27 |
| F | 4 | AR− AD+ As+ | Food Trial | Yes | 23 | 52 |
| F | 6 | AR+ AD+ As+ | Food Trial | No | 42 | 17 |
| M | 17 | AR− AD− As− | Unrestricted Diet | Yes | 56 | 45 |
| F | 17 | AR+ AD+ As− | Steroids | Yes | 49 | 18 |
| M | 5 | AR− AD+ As− | Unrestricted Diet | Yes | 219 | 81 |
| F | 10 | AR+ AD− As− | Unrestricted Diet | No | 36 | 46 |
| M | 14 | AR+ AD+ As+ | Food Trial + Steroids | Yes | 89 | 21 |
| M | 5 | AR+ AD− As− | Food Trial | Yes | 34 | 20 |
| M | 11 | AR+ AD− As− | Unrestricted Diet | Yes | 36 | 41 |
| M | 17 | AR+ AD− As+ | Unrestricted Diet | No | 83 | 87 |
| M | 17 | AR− AD− As− | Unrestricted Diet | Yes | 120 | 44 |
| F | 16 | AR+ AD− As− | Food Trial | Yes | 81 | 63 |
| F | 16 | AR− AD− As− | Unrestricted Diet | Yes | 45 | 37 |
| M | 16 | AR+ AD− As− | Unrestircted Diet | No | 52 | 37 |

Figure 6:
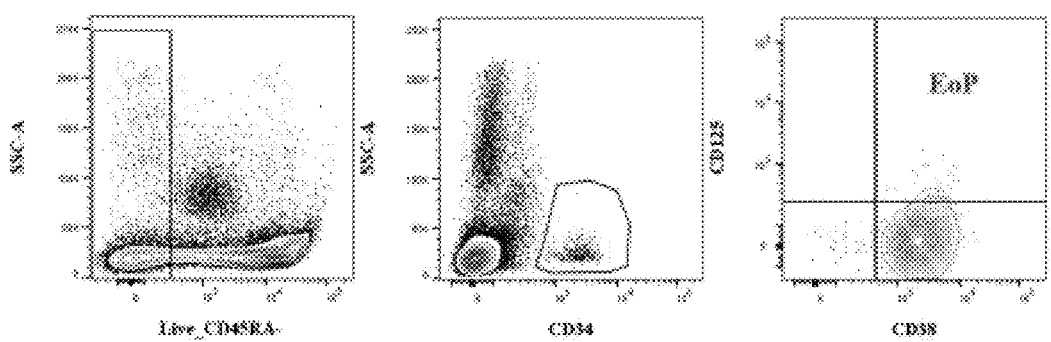
FIG. 6. Graphs showing live CD45RA, CD34, and CD38.

[a]Age at time of endoscopy
[b]Per medical records; AR, allergic rhinitis; AD, atopic dermatitis; As, asthma; PPI, proton pump inhibitor
[c]Therapy at time of endoscopy Identification of human EoP in peripheral blood may be performed as follows:

population was then gated for CD38 and CD125, with double-positive events identified as EoPs (see FIG. 6).

Absolute EoP counts per mL of blood are determined based on number of cell events and the known number of accucount particles in the sample volume (per manufacturer's instructions).

Applicant ascertained whether there were differences in blood EoP levels in patients with active EoE disease versus inactive disease. The median absolute EoP level per mL of blood in patients with active EoE was increased more than two fold over the EoP level in patients with inactive EoE (37.0 [interquartile range, 20.5-49.0] versus 13.5 [5.5-30.3] EoPs per mL of blood, p<0.001 Mann-Whitney, FIG. 1A). Absolute EoP levels also significantly correlated with the esophageal eosinophil level (Spearman r=0.56, p=0.0011, FIG. 1B). Applicant next investigated the ability of EoP levels to serve as a biomarker for EoE disease activity. A receiver operator curve showed an area under the curve of 0.84 (95% CI, 0.70 to 0.98, p=0.0015, FIG. 1C). A cutoff value of less than 15.5 absolute EoPs per mL accurately excluded active disease in 100% of patients. Concurrently, levels equal to or greater than 15.5 absolute EoPs per mL reliably predicted active disease in 74% of patients (sensitivity=100%, specificity=57%, PPV=74%, NPV=100%, $LR^+$=2.3, $LR^-$=0). Using leave-one-out cross-validation and a threshold of 15.5, Applicant found that the mean specificity was 57±3% while retaining 100% sensitivity. These data support the utility of EoP as an excellent disease activity biomarker in patients with EoE.

As peripheral blood EoP levels performed well as a disease activity biomarker, Applicant assessed whether differences in EoP levels existed between different therapeutic groups. Both swallowed steroids and elimination diets, in which disease-triggering foods are avoided, are effective treatments in many pediatric patients with EoE [3, 9]. Most of the patient cohort was on dietary therapy at the time of their endoscopy (Table 1). To investigate the effect of dietary restrictions on blood EoP levels, Applicant subdivided the patients with active EoE disease into two groups, unrestricted diet or restricted diet, at the time of endoscopy. Applicant observed that the median absolute EoP level was significantly increased amongst patients with active EoE on an unrestricted diet versus those on a restricted diet (44.5 [interquartile range, 38.0-72.3] versus 24.0 [17.8-47.8] EoPs per mL of blood, p=0.04, FIG. 1D). Interestingly, esophageal eosinophils levels were similar between patients with active EoE on restricted diet and those on an unrestricted diet (p=0.4, FIG. 1E), suggesting that EoP levels are sensitive to dietary restrictions in patients with active EoE disease.

As EoP levels are elevated in the peripheral blood of adult patients with atopic diseases [5], Applicant investigated whether a history of other allergic diseases was associated with increased blood EoP levels in the population. A clinical history of an atopic disorder (atopic dermatitis, allergic rhinitis, or asthma) did not correlate with EoP elevations and esophageal disease activity (FIG. 2 in the online repository). Additionally, peripheral blood eosinophil counts (n=10) did not correlate with peripheral blood EoP levels (Spearman r=0.16, p=0.65, FIG. 3 in the online repository).

Thus, EoP levels may be used as a disease-monitoring biomarker in patients previously diagnosed with EoE. The current disease monitoring standard dictates that all patients undergo invasive endoscopy with tissue biopsies due to poor correlation between clinical symptoms and tissue inflammation [10]. Any reduction of invasive procedures through the use of less-invasive blood biomarkers would be valuable. Thus, in Applicant's study, 8/14 patients (57%) would have avoided endoscopy due to correctly classified inactive disease. Such a biomarker of "disease inactivity" would be clinically beneficial for this population, as it may alleviate many of the burdens associated with repeated invasive esophageal biopsies.

REFERENCES

1. Bullock, J. Z., et al., Interplay of Adaptive Th2 Immunity with Eotaxin-3/C-C Chemokine Receptor 3 in Eosinophilic Esophagitis. Journal of Pediatric Gastroenterology and Nutrition, 2007. 45: p. 22-31.
2. Blanchard, C., et al., *A striking local esophageal cytokine expression profile in eosinophilic esophagitis*. J Allergy Clin Immunol, 2011. 127(1): p. 208-17, 217 e1-7.
3. Liacouras, C. A., et al., *Eosinophilic esophagitis: updated consensus recommendations for children and adults*. J Allergy Clin Immunol, 2011. 128(1): p. 3-20 e6; quiz 21-2.
4. Konikoff, M. R., et al., Potential of blood eosinophils, eosinophil-derived neurotoxin, and eotaxin-3 as biomarkers of eosinophilic esophagitis. Clin Gastroenterol Hepatol, 2006. 4(11): p. 1328-36.
5. Sehmi, R., et al., Increased Levels of CD34+ Hemopoietic Progenitor Cells in Atopic Subjects. Am J Respir Cell Mol Biol, 1996. 15: p. 645-54.
6. Makowska, J., et al., Recruitment of CD34+ progenitor cells into peripheral blood and asthma severity. Ann Allergy Asthma Immunol, 2008. 101: p. 402-406.
7. Mori, Y., et al., Identification of the human eosinophil lineage-committed progenitor: revision of phenotypic definition of the human common myeloid progenitor. J Exp Med, 2009. 206(1): p. 183-93.
8. Smith, S. G., et al., Thymic stromal lymphopoietin and IL-33 modulate migration of hematopoietic progenitor cells in patients with allergic asthma. J Allergy Clin Immunol, 2015. 135(6): p. 1594-602.
9. Henderson, C. J., et al., Comparative dietary therapy effectiveness in remission of pediatric eosinophilic esophagitis. J Allergy Clin Immunol, 2012. 129(6): p. 1570-8.
10. Martin, L. J., et al., Pediatric Eosinophilic Esophagitis Symptom Scores (PEESS v2.0) identify histologic and molecular correlates of the key clinical features of disease. J Allergy Clin Immunol, 2015. 135: p. 1519-28.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of diagnosing and treating a subject with active or inactive eosinophilic esophagitis (EoE) in a patient suffering from EoE, comprising the steps of
   a. detecting whether a level of eosinophil lineage-committed progenitor (EoP) is elevated in a blood sample obtained from said subject;
   b. diagnosing said subject with active EoE when said EoP level in the sample is elevated above a pre-determined cut-off value and diagnosing said subject with inactive EoE when said EoP level in the sample is below a pre-determined cut-off value; and
   c. treating said subject diagnosed with active EoE;
   wherein when said EoP level is below a cut-off of about 15.5 EoPs per mL (esophageal eosinophils/HPF) of blood, said subject is diagnosed with inactive EoE, and wherein when said EoP level is above a cut-off of about 15.5 EoPs per mL of blood, said subject is diagnosed with active EoE.

2. The method of claim 1, wherein said treatment step comprises administration of steroids, administration of a proton-pump inhibitor, withdrawal of one or more food types, an amino-acid based formula diet, or a combination thereof.

* * * * *